United States Patent [19]

Shinohara et al.

[11] 4,096,161
[45] Jun. 20, 1978

[54] PROCESS FOR THE PREPARATION OF HALOGENOSILANES

[75] Inventors: Toshio Shinohara; Masatoshi Arai; Shoji Ichinohe, all of Annaka, Japan

[73] Assignee: Shin-Etsu Chemical Co., Ltd., Tokyo, Japan

[21] Appl. No.: 742,845

[22] Filed: Nov. 18, 1976

[30] Foreign Application Priority Data

Nov. 26, 1975  Japan .................................. 50/141486

[51] Int. Cl.² ............................. C07F 7/08; C07F 7/12
[52] U.S. Cl. .............................................. 260/448.2 P
[58] Field of Search ................................... 260/448.2 P

[56] References Cited

U.S. PATENT DOCUMENTS 3,646,088   2/1972   Bakassian et al. ............. 260/448.2 P
3,718,682   2/1973   Bakassian et al. ............. 260/448.2 P Primary Examiner—Paul F. Shaver
Attorney, Agent, or Firm—Toren, McGeady and Stanger

[57] ABSTRACT

Halogenosilanes are prepared from an organohalogenosilane and an organopolysiloxane as the starting materials by subjecting them to an intermolecular redistribution reaction in the presence of a monohydrochloride of a hexaalkylphosphotriamide. The thus prepared halogenosilanes, which are different from the starting halogenosilane reactant, are very useful in the silicone industry.

16 Claims, No Drawings

PROCESS FOR THE PREPARATION OF HALOGENOSILANES

BACKGROUND OF THE INVENTION

The present invention relates to a process for preparing halogenosilanes by a redistribution reaction. There are known methods in which two different silicon compounds are subjected to a redistribution reaction in the presence of an amine, such as stearyl amine or aniline or a Lewis acid, such as aluminum chloride or iron(III) chloride to obtain a valuable silicon compound which is different from either of the starting silicon compounds (see U.S. Pat. Nos. 3,065,252 and No. 3,101,361). The prior art methods are disadvantaged, for example, by that the reaction must be carried out under pressure at a high temperature over 150° C. Such reaction conditions cause complicated side reactions to take place simultaneously and, as a result, the yields of the intended silicon compounds will be reduced, while the separation and recovery of the products from the reaction mixtures will sometimes be very difficult.

Furthermore, a redistribution reaction has been proposed between a siloxane reactant and a chlorosilane in the presence of a hexaalkylphosphotriamide (see, for example, U.S. Pat. No. 3,646,088), in which the cleavage of a silicon-oxygen bond takes place and one fragment of the siloxane is combined with the chlorine atom from the chlorosilane, while the other fragment of the siloxane is combined with the residue of the chlorosilane. When this process is employed as a means for preparing the desired chlorosilane, however, it is disadvantaged by low yields because only one fragment of the siloxane is converted to the chlorosilane.

SUMMARY OF THE INVENTION

It is the object of the present invention to provide an effective means to obtain organohalogenosilanes, which are very useful and highly demanded in the silicone industry, from an organopolysiloxane and an organohalogenosilane as the starting materials.

As the result of our research relating to processes of producing, from an organopolysiloxane and a halogenosilane, a valuable halogenosilane product different from the starting halogenosilane, it has been discovered that when these two kinds of the starting silicon compounds are subjected to a redistribution reaction in the presence of a hydrochloride of a hexaalkylphosphotriamide, the intended halogenosilane can easily be obtained in a high yield, without the above-described disadvantages involved in the conventional processes.

Thus, the present invention provides a process for the preparation of an organohalogenosilane product expressed by the general formula $$R^1{}_a SiX_{4-a}$$

where $R^1$ is a hydrogen atom or a substituted or unsubstituted monovalent hydrocarbon group, $a$ is 1, 2 or 3 and X is a halogen atom, by a reaction between an organohalogenosilane reactant expressed by the general formula $$R^2{}_b SiX_{4-b} \tag{I}$$

where $R^2$ is a substituted or unsubstituted monovalent hydrogen group, X is the same as defined above, and $b$ is 0, 1, or 2, always being smaller than the value of the above-defined $a$ and an organopolysiloxane reactant represented by the average unit formula $$(R^1{}_3SiO_{0.5})_p(R^1{}_2SiO)_q(R^1SiO_{1.5})_r(SiO_2)_s \tag{II}$$

where each $R^1$, which may be the same or different, is the same as defined above and $p$, $q$, $r$ and $s$ each are numbers satisfying the requirements of $0 \leq p \leq 1$, $0 \leq q \leq 1$, $0 \leq r \leq 1$, $0 \leq s < 1$ and $(p+q+r+s)=1$, to bring about a redistribution reaction wherein the reaction is carried out in the presence of a monohydrochloride of a hexaalkylphosphotriamide represented by the general formula

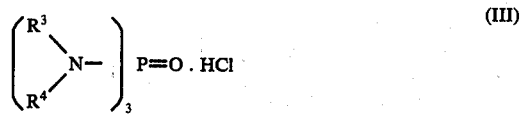

$$\tag{III}$$

where $R^3$ and $R^4$, which may be the same or different, are alkyl groups having 1 to 6 carbon atoms.

DETAILED DESCRIPTION OF THE PREFERRED EMBODIMENTS

The organohalogenosilanes as one of the starting substances expressed by formula (I) above are exemplified by dimethyldichlorosilane, methyltrichlorosilane, diphenyldichlorosilane, phenyltrichlorosilane, vinyltrichlorosilane, methylethyldichlorosilane, ethyltrichlorosilane and tetrachlorosilane.

The organopolysiloxanes useful as the other of the starting substances in accordance with the present invention are represented by formula (II), in which the monovalent hydrocarbon groups denoted by $R^1$ include saturated and unsaturated aliphatic hydrocarbon groups, aryl groups and aralkyl groups as well as the substituted groups thereof by halogen atoms, cyano groups and other substituents. Further, in formula (II), $p,q,r$ and $s$, being numbers satisfying the specified requirements, represent mole fractions of respective siloxane units.

Illustrative of the organopolysiloxanes are hexaorganodisiloxanes; octaorganotrisiloxanes; linear organopolysiloxanes having at least 4 silicon atoms, each terminal group of which is a triorganosilyl group; cyclic organopolysiloxanes, such as hexaorganocyclotrisiloxanes and octaorganocyclotetrasiloxanes; branched and crosslinked oranopolysiloxanes having siloxane units represented by the formulas $R^1{}_3SiO_{0.5}$, $R^1{}_2SiO$ and $R^1SiO_{1.5}$; branched and crosslinked organopolysiloxanes having siloxane units represented by the formula $SiO_2$ in addition to the above siloxane units; and organohydrogenpolysiloxanes derived from the foregoing organopolysiloxanes by replacing part of the organic groups bonded directly to the silicon atoms with hydrogen atoms. As specific examples of such organopolysiloxanes, there can be mentioned hexamethyldisiloxane, 1,1,3,3-tetramethyl-1,3-divinyldisiloxane, 1,1,3,3-tetramethyldisiloxane, 1,1,3,3-tetramethyl-1,3-di-n-butyldisiloxane, 1,1,3,3-tetramethyl-1,3-diethynyldisiloxane, 1,1,3,3-tetraphenyl-1,3-dimethyldisloxane, 1,1,3,3-tetramethyl-1,3-diphenyldisiloxane, octamethyltrisiloxane, 1,1,3,3-tetramethyldisiloxane, hexamethylcyclotrisiloxane and octamethylcyclotetrasiloxane.

The redistribution reaction in accordance with the present invention is carried out in the presence of a hydrochloride of a hexaalkylphosphotriamide expressed by formula (III) above, which serves as a catalyst to accelerate the reaction. The charge of the catalyst into a reaction vessel can be carried out in the following manners. For example, the prepared hydrochloride is introduced into the reaction vessel together with the two starting compounds. As another example, the hexaalkylphosphotriamide is introduced into the reaction vessel together with the two starting compounds, followed by addition of hydrogen chloride or hydrochloric acid as a hydrochloride-forming agent. As a further example, the hexaalkylphosphotriamide is introduced into the reaction vessel together with the two starting compounds, followed by addition of water, an alcohol, an inorganic or organic acid or amine as a hydrochloride-forming agent to generate hydrogen chloride in situ by the partial decomposition of the starting halogenosilane.

The amount of the hydrochloride as the catalyst is not narrowly critical and may range from 0.001 to 80% by weight based on the total weight of the starting siloxane and silane. Preferably from 0.1 to 10% of the catalyst based on the total weight of the siloxane and silane is employed.

Hexaalkylphosphotriamides can form two kinds of hydrochlorides, i.e., monohydrochloride and dihydrochloride, by reaction with 1 or 2 moles of hydrogen chloride, of which the former hydrochloride is especially suitable in the redistribution reaction of the present invention. Therefore, when the in situ formation of the hydrochloride is intended as described above, the amount of the hydrochloride-forming agent, e.g., hydrogen chloride, hydrochloric acid, water or an alcohol, should be limited so that the formation of the dihydrochloride may be avoided.

In practicing the process of the invention as described above, it may be possible that the hexaalkylphosphotriamide which has not been converted to the hydrochloride is present in the reaction vessel. The reaction temperature may range from 0° to 200° C, preferably from 20° to 150° C. Under these reaction conditions, the intended redistribution reaction can proceed rapidly. The molar ratio of the starting reactants may be appropriately chosen depending on the kinds of the starting reactants and according to the stoichiometry of the intended redistribution reaction.

The following examples are illustrative of the practice of the present invention and are not intended for limitation. In the examples, percentages are all by weight.

EXAMPLE 1

To a mixture consisting of 48.7 g of hexamethyldisiloxane, 30.0 g of methyltrichlorosilane and 2.6 g (0.0145 mole) of hexamethylphosphotriamide was added 0.20 g (0.0111 mole) of water, and the resulting mixture was heated at 80° C for 4 hours. Here, part of the methyltrichlorosilane was hydrolyzed by the added water to generate hydrogen chloride, which in turn formed the monohydrochloride of the hexamethylphosphotriamide. The resultant reaction mixture was analyzed and it was found that 57.4 g of trimethylchlorosilane was produced with 88% yield based on the hexamethyldisiloxane.

For comparison, a similar procedure was repeated except that the addition of water was omitted and, as a result, the yield of trimethylchlorosilane based on the hexamethyldisiloxane was 40%.

EXAMPLE 2

To a mixture consisting of 93.2 g of 1,1,3,3-tetramethyl-1, 3-divinyldisiloxane, 64.5 g of dimethyldichlorosilane and 4.7 g of hexaethylphosphotriamide was added 0.40 g of water, and the resulting mixture was heated at 100° C for 4 hours. The reaction mixture was then analyzed and it was found that 102.6 g of dimethylvinylchlorosilane was produced with 91% yield based on the 1,1,3,3-tetramethyl-1, 3-divinyldisiloxane.

EXAMPLE 3

To a mixture consisting of 134.3 g of 1,1,3,3-tetramethyldisiloxane, 129.0 g of dimethyldichlorosilane and 8.0 g of hexamethylphosphotriamide was added 0.66 g of water, and the resulting mixture was heated at 40° C for 4 hours. The reaction mixture was then analyzed and it was found that 113 g of dimethylchlorosilane was produced with 60% yield based on the 1,1,3,3-tetramethyldisiloxane.

EXAMPLE 4

To a mixture consisting of 147.9 g of 1,1,3,3-tetramethyl-1, 3-di-n-butyldisiloxane, 80.6 g of phenyltrichlorosilane and 6.9 g of hexamethylphosphotriamide was added 0.57 g of water, and the resulting mixture was heated at 130° C for 6 hours. The reaction mixture was then analyzed and it was found that 150 g of n-butyldimethylchlorosilane was produced with 83% yield based on the 1,1,3,3-tetramethyl-1, 3-di-n-butyldisiloxane.

EXAMPLE 5

To a mixture consisting of 54.7 g of 1,1,3,3-tetramethyl-1, 3-diethynyldisiloxane, 42.3 g of phenyltrichlorosilane and 2.9 g of hexamethylphosphotriamide was added 0.24 g of water, and the resulting mixture was heated at 60° C for 4 hours. The reaction mixture was then analyzed and it was found that 67.7 g of dimethylethynylchlorosilane was produced with 95% yield based on the 1,1,3,3-tetramethyl-1, 3-diethynyldisiloxane.

EXAMPLE 6

To a mixture consisting of 23.7 g of octamethyltrisiloxane, 44.8 g of methyltrichlorosilane and 3.4 g of hexamethylphosphotriamide was added 0.068 g of water, and the resulting mixture was heated at 80° C for 4 hours. The reaction mixture was then analyzed and it was found that 16.2 g and 9.6 g of trimethylchlorosilane and dimethyldichlorosilane, respectively, were produced with yields of 74.8% and 74.5%, respectively, based on the octamethyltrisiloxane.

EXAMPLE 7

To a mixture consisting of 48.7 g of hexamethyldisiloxane, 30.0 g of methyltrichlorosilane and 2.6 g of hexamethylphosphotriamide was added 0.50 g of methanol, and the resulting mixture was heated at 80° C for 4 hours. Here, part of the methyltrichlorosilane was alcoholyzed by the added methanol to generate hydrogen chloride, which in turn formed the monohydrochloride of the hexamethylphosphotriamide. The reaction mixture was then analyzed and it was found that 53.5 g of trimethylchlorosilane was produced with 82% yield based on the hexamethyldisiloxane.

EXAMPLE 8

To a mixture consisting of 14.8 g of octamethylcyclotetrasiloxane, 37.4 g of methyltrichlorosilane and 2.6 g of hexamethylphosphotriamide was added 0.52 g of water, and the resulting mixture was heated at 80° C for 4 hours. The reaction mixture was then analyzed and it was found that 19.6 g of dimethyldichlorosilane was produced with 76% yield based on the octamethylcyclotetrasiloxane.

EXAMPLE 9

Hydrogen chloride gas was passed through 50 g of hexamethylphosphotriamide (HMPA) in a flask, to form a white crystalline precipitate, which was then taken out of the reaction mixture by filtration. The amount of thus obtained precipitate was 12.5 g. (This precipitate is hereinafter called crystalline salt I).

From the filtrate obtained above, a second white crystalline matter was precipitated by addition of n-hexane. The amount of this second precipitate separated by filtration was 16.4 g. (This second precipitate is called crystalline salt II, and the filtrate obtained by the second filtration is called liquid III). Crystalline salts I and II were dried in a desiccator under reduced pressure.

The elementary analyses, including the determination of chlorine, gave the results that the crystalline salts I and II and liquid III were, respectively, dihydrochloride of HMPA, i.e., HMPA.(HCl)$_2$; monohydrochloride of HMPA, i.e., HMPA.HCl; and HMPA diluted with n-hexane.

Using each of these compounds as the catalyst, i.e., (a) crystalline salt I, (b) crystalline salt II, (c) liquid III and (d) mixture of liquid III and water, in an amount as indicated in the following table, a redistribution reaction was conducted between 93.2 g of 1,1,3,3-tetramethyl-1, 3-divinyldisiloxane and 64.5 g of dimethyldichlorosilane with heating at 100° C for 4 hours. As a result, dimethylvinylchlorosilane was obtained with the yields as indicated also in the table.

Table

| Catalyst | Amount* | Yield** |
|---|---|---|
| (a) Crystalline salt I | 5.0 % | 26 % |
| (b) Crystalline salt II | 5.0 % | 92 % |
| (c) Liquid III | ***5.0 % | 35 % |
| (d) Mixture of: | | |
| Liquid III | ***5.0 % | |
| Water | 0.25 % | 90 % |

*Based on the total amount of 1,1,3,3-tetramethyl-1, 3-divinyldisiloxane and dimethyldichlorosilane.
**Based on 1,1,3,3-tetramethyl-1, 3-divinyldisiloxane.
***AS non-diluted HMPA.

What is claimed is:

1. A process for the preparation of an organohalogenosilane product expressed by the general formula $$R^1_a SiX_{4-a}$$

where $R^1$ is a hydrogen atom or a substituted or unsubstituted monovalent hydrocarbon group, $a$ is 1, 2 or 3 and X is a halogen atom, by a reaction between an organohalogenosilane reactant expressed by the general formula $$R^2_b SiX_{4-b}$$

where $R^2$ is a substituted or unsubstituted monovalent hydrocarbon group, X is the same as defined above, and $b$ is 0, 1, or 2, always being smaller than the value of the above-defined $a$ and an organopolysiloxane reactant represented by the average unit formula $$(R^1_3 SiO_{0.5})_p (R^1_2 SiO)_q (R^1 SiO_{1.5})_r (SiO_2)_s$$

where each $R^1$, which may be the same or different, is the same as defined above and $p$, $q$, $r$ and $s$ each are numbers satisfying the requirements of $0 \leq p \leq 1$, $0 \leq q \leq 1$, $0 \leq r \leq 1$, $0 \leq s < 1$ and $(p+q+r+s)=1$, to bring about a redistribution reaction wherein the reaction is carried out in the presence of a monohydrochloride of a hexaalkylphosphotriamide represented by the general formula

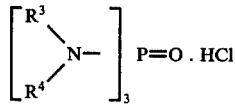

where $R^3$ and $R^4$, which may be the same or different, are alkyl groups having 1 to 6 carbon atoms.

2. The process according to claim 1 wherein the organopolysiloxane reactant is a hexaorganodisiloxane.

3. The process according to claim 1 wherein the organopolysiloxane reactant is an octaorganotrisiloxane.

4. The process according to claim 1 wherein the organopolysiloxane reactant is a tetraorganodisiloxane.

5. The process according to claim 1 wherein the organopolysiloxane reactant is a cyclic organopolysiloxane having 3 or 4 silicon atoms.

6. The process according to claim 1 wherein the organohalogenosilane reactant is an organotrichlorosilane.

7. The process according to claim 1 wherein the organohalogenosilane reactant is a diorganodichlorosilane.

8. The process according to claim 1 wherein the hexaalkylphosphotriamide is hexamethylphosphotriamide.

9. The process according to claim 1 wherein the hexaalkylphosphotriamide is hexaethylphosphotriamide.

10. The process according to claim 1 wherein the monohydrochloride of the hexaalkylphosphotriamide is used in an amount of 0.001 to 80% by weight based on the total amount of the organohalogenosilane reactant and the organopolysiloxane reactant.

11. The process according to claim 1 wherein the monohydrochloride of the hexaalkylphosphotriamide is used in an amount of 0.1 to 10% by weight based on the total amount of the organohalogenosilane reactant and the organopolysiloxane reactant.

12. The process according to claim 1 wherein the redistribution reaction is carried out at a temperature in the range of from 0° to 200° C.

13. The process according to claim 1 wherein the redistribution reaction is carried out at a temperature in the range of from 20° to 150° C.

14. The process according to claim 1 wherein the monohydrochloride of the hexaalkylphosphotriamide prepared is admixed with the organohalogenosilane reactant and the organopolysiloxane reactant.

15. The process according to claim 1 wherein the monohydrochloride of the hexaalkylphosphotriamide is formed in situ by the addition of a hydrochloride-forming agent into the mixture of the organohalogenosilane reactant, the organopolysiloxane reactant and the hexaalkylphosphotriamide.

16. The process according to claim 15 wherein the hydrochloride-forming agent is water or an alcohol.

* * * * *